(12) United States Patent
Biener et al.

(10) Patent No.: US 7,100,610 B2
(45) Date of Patent: Sep. 5, 2006

(54) BREATHING MASK FOR FEEDING A BREATHING GAS TO A MASK USER AND DISCHARGE DEVICE FOR DISCHARGING BREATHING GAS

(75) Inventors: Achim Biener, Munich (DE); Bernd Lang, Grafelfing (DE)

(73) Assignee: MAP Medizintechnologie GmbH, Martinsried (DE)

( * ) Notice: Subject to any disclaimer, the term of this patent is extended or adjusted under 35 U.S.C. 154(b) by 196 days.

(21) Appl. No.: 10/221,574

(22) PCT Filed: Oct. 16, 2001

(86) PCT No.: PCT/EP01/11954

§ 371 (c)(1),
(2), (4) Date: Jan. 28, 2003

(87) PCT Pub. No.: WO02/32491

PCT Pub. Date: Apr. 25, 2002

(65) Prior Publication Data

US 2003/0221691 A1 Dec. 4, 2003

(30) Foreign Application Priority Data

Oct. 19, 2000 (DE) ................................. 100 51 891
Oct. 19, 2000 (DE) ........................... 200 17 940 U

(51) Int. Cl.
*A62B 18/02* (2006.01)

(52) U.S. Cl. ........................... 128/206.21; 128/205.25; 128/206.12

(58) Field of Classification Search ........... 128/206.21, 128/205.25, 206.12, 207.11, 207.14, 207.18
See application file for complete search history.

(56) References Cited

U.S. PATENT DOCUMENTS

| 781,516 | A | 1/1905 | Guthrie |
| 812,706 | A | 2/1906 | Warbasse |
| 1,081,745 | A | 12/1913 | Johnston et al. |
| 1,192,186 | A | 7/1916 | Greene |
| 1,653,572 | A | 12/1927 | Jackson |
| 1,926,027 | A | 9/1933 | Biggs |
| 2,123,353 | A | 7/1938 | Catt |
| 2,245,969 | A | 6/1941 | Francisco et al. |

(Continued)

FOREIGN PATENT DOCUMENTS

AU 91/77110 B 11/1991

(Continued)

OTHER PUBLICATIONS

European Search Report (Dec. 21, 2004).

*Primary Examiner*—Anhtuan T. Nguyen
*Assistant Examiner*—Darwin P. Erezo
(74) *Attorney, Agent, or Firm*—Nixon & Vanderhye P.C.

(57) ABSTRACT

The invention relates to a breathing mask for feeding a breathing gas to a mask user and a discharging device for discharging breathing gas from an inner mask area defined by a breathing mask. The inventive breathing mask comprises a sealing lip device for sealing a mask bearing area, a mask base body for creating a space within the mask and a connecting device for connecting at least one breathing gas line, the mask base body and/or the connecting device being provided with at least one decoupling structure made of elastomer material. It is possible to obtain in an advantageous manner a relative movement between a peripheral base area on the side of the base body of the mask associated with the sealing lip device and the breathing gas line within a sufficient area of movement.

8 Claims, 11 Drawing Sheets

U.S. PATENT DOCUMENTS

| | | |
|---|---|---|
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,590,006 A | 3/1952 | Gordon |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,750,333 A | 8/1973 | Vance |
| 3,752,157 A | 8/1973 | Malmin |
| 3,779,164 A | 3/1974 | Rollins |
| 3,796,216 A | 3/1974 | Schwarz |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,120,302 A | 10/1978 | Ziegler |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| D285,496 S | 9/1986 | Berman |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| H397 H | 1/1988 | Stark |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A * | 4/1990 | Kopala et al. ......... 128/207.18 |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,322,059 A * | 6/1994 | Walther ................. 128/205.23 |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |

| | | | | | | |
|---|---|---|---|---|---|---|
| 5,649,532 A | 7/1997 | Griffiths | | AU | 95/16178 B | 7/1995 |
| 5,649,533 A | 7/1997 | Oren | | AU | 9459430 | 2/1996 |
| 5,655,520 A | 8/1997 | Howe et al. | | AU | A 32914/95 | 2/1996 |
| 5,655,527 A | 8/1997 | Scarberry et al. | | AU | A 41018/97 | 4/1998 |
| 5,657,493 A | 8/1997 | Ferrero et al. | | AU | A 89312/98 | 1/1999 |
| 5,657,752 A | 8/1997 | Landis et al. | | CA | 1039144 | 9/1928 |
| 5,662,101 A | 9/1997 | Ogden et al. | | EP | 0 252 052 A1 | 1/1988 |
| 5,666,946 A | 9/1997 | Langenback | | EP | 0 264 772 A1 | 4/1988 |
| 5,685,296 A | 11/1997 | Zdrojkowski et al. | | EP | 0427474 A2 | 5/1991 |
| 5,687,715 A | 11/1997 | Landis et al. | | EP | 0 462 701 A1 | 12/1991 |
| 5,715,814 A | 2/1998 | Ebers | | EP | 178 925 A2 | 4/1996 |
| 5,724,965 A | 3/1998 | Handke et al. | | EP | 0 747 078 A2 | 12/1996 |
| 5,746,201 A | 5/1998 | Kidd | | EP | 0 821 978 | 2/1998 |
| 5,813,423 A | 9/1998 | Kirchgeorg | | GB | 1395391 | 5/1975 |
| 5,832,918 A | 11/1998 | Pantino | | GB | 1 467 828 | 3/1977 |
| D402,755 S | 12/1998 | Kwok | | GB | 2145335 A | 3/1985 |
| 5,921,239 A | 7/1999 | McCall et al. | | GB | 2147506 A | 5/1985 |
| 5,937,851 A | 8/1999 | Serowski et al. | | GB | 2 164 569 A | 3/1986 |
| D423,096 S | 4/2000 | Kwok | | GB | 2 186 801 | 8/1987 |
| 6,044,844 A | 4/2000 | Kwok et al. | | GB | 2 267 648 A | 12/1993 |
| D428,987 S | 8/2000 | Kwok | | WO | WO 80/01044 | 5/1980 |
| 6,098,205 A | 8/2000 | Schwartz et al. | | WO | WO 82/03548 | 10/1982 |
| 6,112,746 A | 9/2000 | Kwok et al. | | WO | WO 86/06969 | 12/1986 |
| 6,119,693 A * | 9/2000 | Kwok et al. ............ 128/207.11 | | WO | WO 87/01950 | 4/1987 |
| 6,123,071 A | 9/2000 | Berthon-Jones et al. | | WO | WO 92/15353 | 9/1992 |
| 6,152,137 A | 11/2000 | Schwartz et al. | | WO | WO 93/01854 | 2/1993 |
| D439,326 S | 3/2001 | Hecker et al. | | WO | WO 94/16759 | 8/1994 |
| D443,355 S | 6/2001 | Gunaratnam et al. | | WO | WO 94/20051 | 9/1994 |
| 6,257,237 B1 | 7/2001 | Suzuki | | WO | WO 96/17643 | 6/1996 |
| 6,341,606 B1 | 1/2002 | Bordewick et al. | | WO | WO 96/25983 | 8/1996 |
| 6,374,826 B1 * | 4/2002 | Gunaratnam et al. .. 128/206.27 | | WO | WO 96/39206 | 12/1996 |
| 6,397,847 B1 | 6/2002 | Scarberry et al. | | WO | WO 97/07847 | 3/1997 |
| 6,463,931 B1 | 10/2002 | Kwok et al. | | WO | WO 97/41911 | 11/1997 |
| D468,823 S | 1/2003 | Smart | | WO | WO 98/04310 | 2/1998 |
| 6,520,182 B1 | 2/2003 | Gunaratnam | | WO | W0 98/11930 | 3/1998 |
| 6,532,961 B1 * | 3/2003 | Kwok et al. ............ 128/206.21 | | WO | WO 9812965 | 4/1998 |
| 6,557,556 B1 | 5/2003 | Kwok | | WO | WO 98/18514 | 5/1998 |
| 6,595,214 B1 | 7/2003 | Hecker | | WO | WO 98/24499 | 6/1998 |
| D484,237 S | 12/2003 | Lang et al. | | WO | WO 98/26829 | 6/1998 |
| 6,679,261 B1 | 1/2004 | Lithgow | | WO | WO 98/26830 | 6/1998 |
| 6,691,707 B1 | 2/2004 | Gunaratnam et al. | | WO | WO 9834665 | 8/1998 |
| 6,691,708 B1 | 2/2004 | Kwok et al. | | WO | WO 9943375 | 9/1999 |
| D492,992 S | 7/2004 | Guney et al. | | WO | WO 99/58181 | 11/1999 |
| 2003/0019496 A1 | 1/2003 | Kopacko et al. | | WO | WO 00/57942 | 10/2000 |
| 2003/0034034 A1 | 2/2003 | Kwok et al. | | WO | WO 00/78384 | 12/2000 |
| 2003/0062048 A1 | 4/2003 | Gradon | | WO | WO 0078381 | 12/2000 |
| 2003/0089373 A1 | 5/2003 | Gradon | | WO | WO 01/97892 | 12/2001 |
| 2003/0221691 A1 | 12/2003 | Biener et al. | | WO | WO 2004/022145 | 3/2004 |
| 2004/0045550 A1 | 3/2004 | Lang et al. | | WO | WO 2004022144 | 3/2004 |
| 2004/0045551 A1 | 3/2004 | Eaton | | WO | WO 2004022145 | 3/2004 |
| 2004/0177850 A1 | 9/2004 | Gradon | | WO | WO 2004/078228 | 9/2004 |

FOREIGN PATENT DOCUMENTS

AU  94/64816 B  12/1994

\* cited by examiner

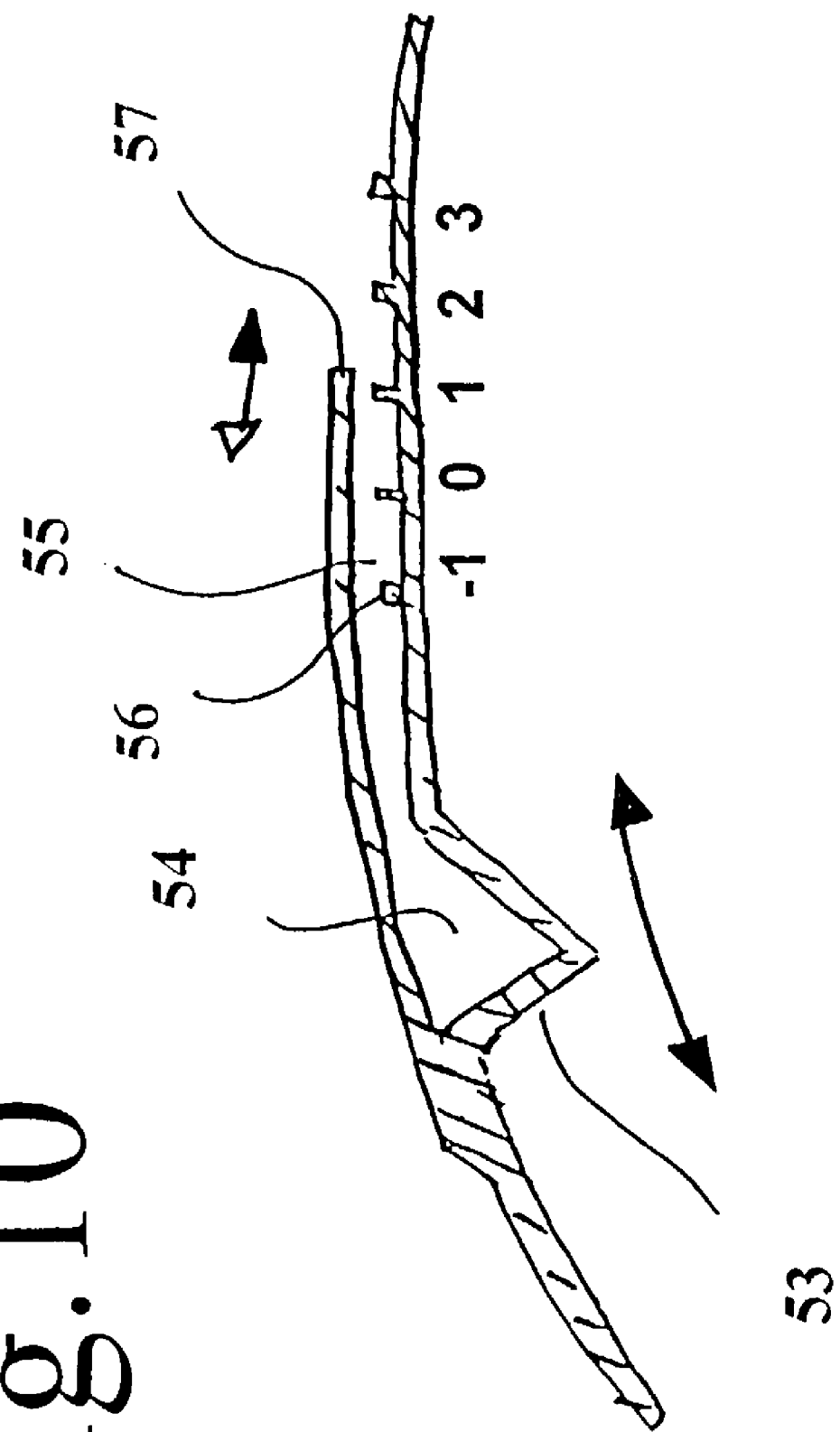

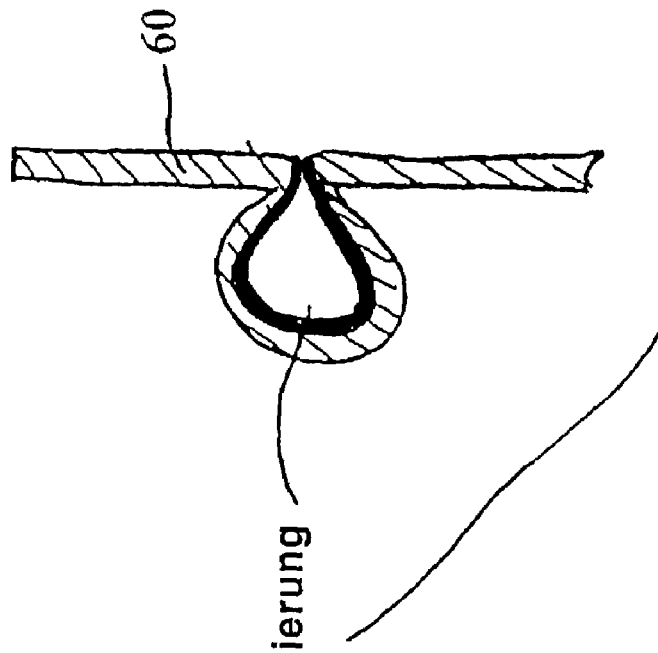
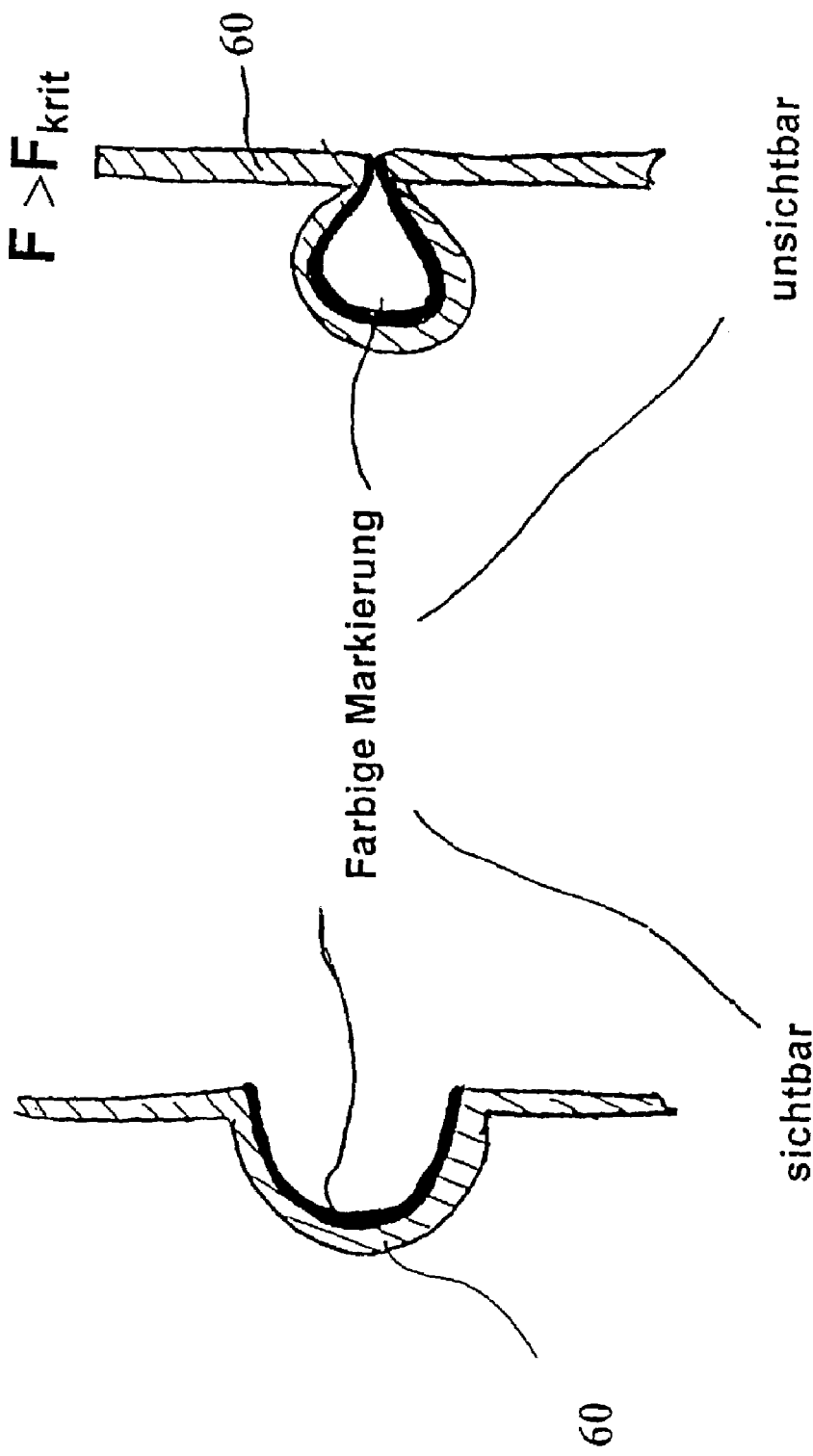

BREATHING MASK FOR FEEDING A BREATHING GAS TO A MASK USER AND DISCHARGE DEVICE FOR DISCHARGING BREATHING GAS

This application is the National Phase of International Application PCT/EP01/11954 filed Oct. 16, 2001 which designated the U.S. and that International Application was not published under PCT Article 21(2) in English.

The present invention refers to a breathing mask for supplying a breathing air to a user of a mask and it refers to a discharge means for discharging breathing gas.

Breathing masks of this type are used in particular in the medical sector, e.g. in the sector of sleep medicine for treating breathing disorders relating to sleep.

Usually, these masks comprise a sealing lip means for sealing a mask rest zone against the atmosphere. In nose masks, the mask rest zone extends from the upper lip portion into the facial portion adjoining the side of the nose of the user of the mask and from there to the area of the bridge of the nose. The sealing lip means is usually made of an elastomer material and pressed against the mask rest zone via a head band arrangement by exerting a predetermined pressure.

In particular in the long-term use of breathing masks of this type, the problem occurs that the required sealing effect can only be achieved at comparatively high mask pressure forces. Due to the required high mask press forces, the comfort of wearing the mask is affected. Moreover, there is a risk of bruises being generated in the area of the mask rest zone.

Thus, the object of the invention is to provide a breathing mask for supplying a breathing gas, which is characterized by a sufficiently high tightness and by a high comfort when wearing the mask.

This object is achieved according to the invention by a breathing mask for supplying a breathing mask to a user of the mask, comprising a sealing lip means for sealing a mask rest zone, a mask base body for forming a mask interior space and a connection means for connecting at least one breathing gas line, wherein the mask base body and/or the connection means are provided with at least one de-coupling structure formed of an elastomer material, which allows a relative movement between a circumferential foot portion of the sealing lip means connected to the mask base body and the breathing gas line at a tilt angle range of less than 5°.

Thus, it is achieved in an advantageous manner to obtain a sufficient sealing effect at a reduced mask holding force in a reliable manner, since even when moving the head of the user of the mask, forces or momentums cannot be transferred via the breathing gas line onto the sealing lip means. In a further advantageous manner, a relative movement between the sealing lip means resting on the face of the user of the mask and a breathing gas line preferably fixed on the front end side (e.g. by a hose holding bracket formed on a reinforcement frame) becomes possible.

The de-coupling structure is according to an especially preferred embodiment of the invention formed by a bellows or roller bellows structure. This bellows or roller bellows structure is preferably formed by using a core element which is integral with the sealing lip means.

According to an especially preferred embodiment of the invention, the bellows or roller bellows structure is formed at the connection means. This bellows or roller bellows structure can be provided with hinge characteristics by zones with adapted wall thickness, by means of which rotational and tilt momentums as well as axial movements of the breathing gas mask do not lead to the generation of possible forces on the sealing lip means.

An also especially preferred embodiment of the invention is given in that the de-coupling structure is formed on the mask base body. This makes it possible to avoid the transfer of undesired forces onto the sealing lip means and at the same time to sufficiently de-couple possible movements of the mask base body relative to the sealing lip means.

An embodiment of the invention that is especially advantageous in view of low operating noises is given in that at least one channel means is provided in the area of the de-coupling structure. This channel means is responsible for creating a connection between the interior of the mask and the atmosphere.

The channel means is preferably formed by a passage opening. The passage opening preferably has a cross section which is adapted to predetermined pressure/volume flow characteristics.

An especially silent discharge is achieved according to the invention in that the channel means tapers step-wise or continuously in the flow direction regarding its cross section.

An embodiment of the invention that is also advantageous in view of a low noise emission is given in that a sharp opening edge is formed in an outlet opening section of the channel means. A section of the smallest cross section is preferably defined in the channel means, wherein the length of the section of the smallest cross section is smaller than 2 mm. It is possible in an advantageous manner that the channel geometry is designed in a manner that the smallest cross section of the channel means is formed in a membrane element. Thereby the coupling of possible body sound events into the mass structure is further reduced. The diameter of the membrane element is preferably 30% larger than the diameter of the throttle passage opening formed therein.

The movable coupling of the sealing lip means is preferably implemented in that the de-coupling structure extends in the mask base body in the circumferential direction of the sealing lip means along a transitional portion between a foot portion of the sealing lip means and is formed by at least one circumferential fold or a roller bellows structure.

According to a further aspect of the present invention, and preferably in combination with the above-described measure, a breathing mask adapted to the individual face structure of the user is provided, which has a forehead rest means for supporting the mask in the forehead or nose bridge area of the person, and which comprises a reinforcement element for reinforcing the breathing mask with a first reinforcement section associated to the portion of the sealing lip means and a second reinforcement section associated to the forehead rest portion, wherein the relative position of the two reinforcement sections to one another is adjustably variable.

Thus, it becomes possible in an advantageous manner to obtain an optimal surface pressure distribution for the respective face structure of the user of the mask in the area of the sealing lip zone and in the area of the forehead area.

An advantageous embodiment of the invention with respect to a simple handling is given in that both reinforcement sections are coupled to one another via a hinge means. The hinge means may in an advantageous manner be formed by a film hinge means.

According to an especially preferred embodiment of the invention, a fixing means is provided for fixing the two reinforcement section in a required relative position. The fixing means comprises in an advantageous manner a fixing mechanism, in particular a catch mechanism. Preferably, a plurality of predetermined catch positions can be selected.

As an alternative, or in combination with this measure, it is also possible to form the fixing means by using means for fixing by adhesion, welding or chemical reaction.

An especially advantageous embodiment of the invention in view of manufacturing points of view is given in that the two reinforcement sections are formed integrally. Thus, it is possible to form the two reinforcement section e.g. of a thermoplastic plastic material by using an only two-piece shaping tool. The two reinforcement sections may be injection-molded in a direction advantageous in view of removal from the mold.

The reinforcement element is preferably shaped frame or skeleton-like or at least in the area of the sealing lip element in a bell-shaped manner. In the case of a skeleton or frame-like design, the individual web sections preferably have a substantially profile cross section. A high rigidity is achieved by a low dead weight of the reinforcement element.

The first reinforcement or frame section preferably has a contour substantially corresponding to the mask rest zone. The second reinforcement or frame section preferably extends up to a portion located in the application position of the mask above the eyebrow of the user of the mask.

An embodiment of the invention that is especially advantageous when using an elastomer mask base body is provided in that the reinforcement element is provided with coupling sections for coupling a head band means. This makes it possible to introduce the mask half forces without an inadmissible deformation of the mask.

The reinforcement element is preferably formed of a plastic material. As an alternative, or in combination therewith, it is possible to make the reinforcement element of a metal material in particular of a bendable wire or profile material. It is also possible to form the reinforcement element of an alt least locally thermo-deformable material, it particular a thermoplastic material having a rigid inset.

It is in particular possible to provide a wire inset in the area of the bending-neutral zone of the profile material.

The profile material preferably comprises at least one rigid lead, e.g. made of a wire material. It is possible to enable at least locally a deformation of the profile material, e.g. by heating up the material so that a further adaptability of the reinforcement or frame element to the face structure is possible.

An especially advantageous adaptability of the breathing mask to the face structure of the user of the mask is achieved according to an especially advantageous embodiment of the invention in that the breathing mask comprises a mask base body made of an elastomer material. Thus, it becomes possible to affect the course of the sealing lip zone and the surface pressing distribution in this zone by an arbitrary deformation of the first reinforcement section.

In an advantageous manner the forehead rest means comprises a rest element which is formed of an elastomer material.

An especially advantageous embodiment according to the invention in terms of hygiene is given in that the sealing lip means is formed integrally with the mask base body. This integral design can be achieved by the common formation in a shaping tool or by adhering the sealing lip means to the mask base body preferably by including a reinforcement means. It is also possible to form the mask base body and the sealing lip means and preferably also the padding members of the forehead rest means in the course of a vulcanization process.

According to a special aspect of the present invention, the padding members of the forehead means are preferably formed integrally with the sealing lip means and/or the mask base body. In the case of a multi-piece design of the mask it is possible to couple the sealing lip means to the mask body via the reinforcement element. The connection portion between the mask base body and the forehead rest means may be effective as an elastomer hinge structure.

The reinforcement element is, according to an especially preferred embodiment of the invention releasably coupled with the sealing lip means and/or the mask base body. Thus it becomes possible in an advantageous manner to use the reinforcement element a plurality of times. The reinforcement element is preferably coupled via a catch or engagement profile structure with the mask base body.

The reinforcement element preferably consists of a plurality of pieces. In an advantageous manner, the mask base body is made of a transparent or translucent elastomer material. An especially favorable embodiment of the invention in view of a high comfort of wearing the mask is given in that the sealing lip means has a satin-like mat surface. By the realization of so-called lotus flower structures, a cleaning structure improved in terms of hygiene is achieved.

The hinge fixation can preferably also be implemented reversibly, e.g. by hot glue or be chemically releasable adhesives. It is also possible to provide thermo-deformable structure especially in the area of the hinge portion, said structures being repeatedly plastically deformable and allowing another adjustment of the relative position of the two reinforcement of frame section e.g. by the supply of heat.

It is also possible to form a plurality of hinge or adjustment zones in the reinforcement element or in the frame structure thereof so that for instance also adjustment possibilities for adaptation to the individual curvature of the forehead, the width of the nose bridge and the upper lip structure are possible.

In particular when forming the reinforcement element as a locally deformable structure, a sufficient strength can be acheived at a small space in that the reinforcement element is formed of a compound material. A wire/thermoplastic compound material is particularly suitable as a compound material.

The adjustability of the at least two reinforcement or frame section with respect to each other can also be obtained according to the invention in that two reinforcement of frame sections can be joined in different coupling positions, e.g. be corresponding permutatably connectable joining portions or selectable joining elements.

Further details can be derived from the following description in connection with the drawing.

FIG. 10 shows a simplified sectional view for explaining a further embodiment of a channel means for discharging breathing gas;

FIG. 11a and FIG. 11b show sketches for explaining the structure of a deformable structure suitable as a power and/or pressure display means;

Figure 1:
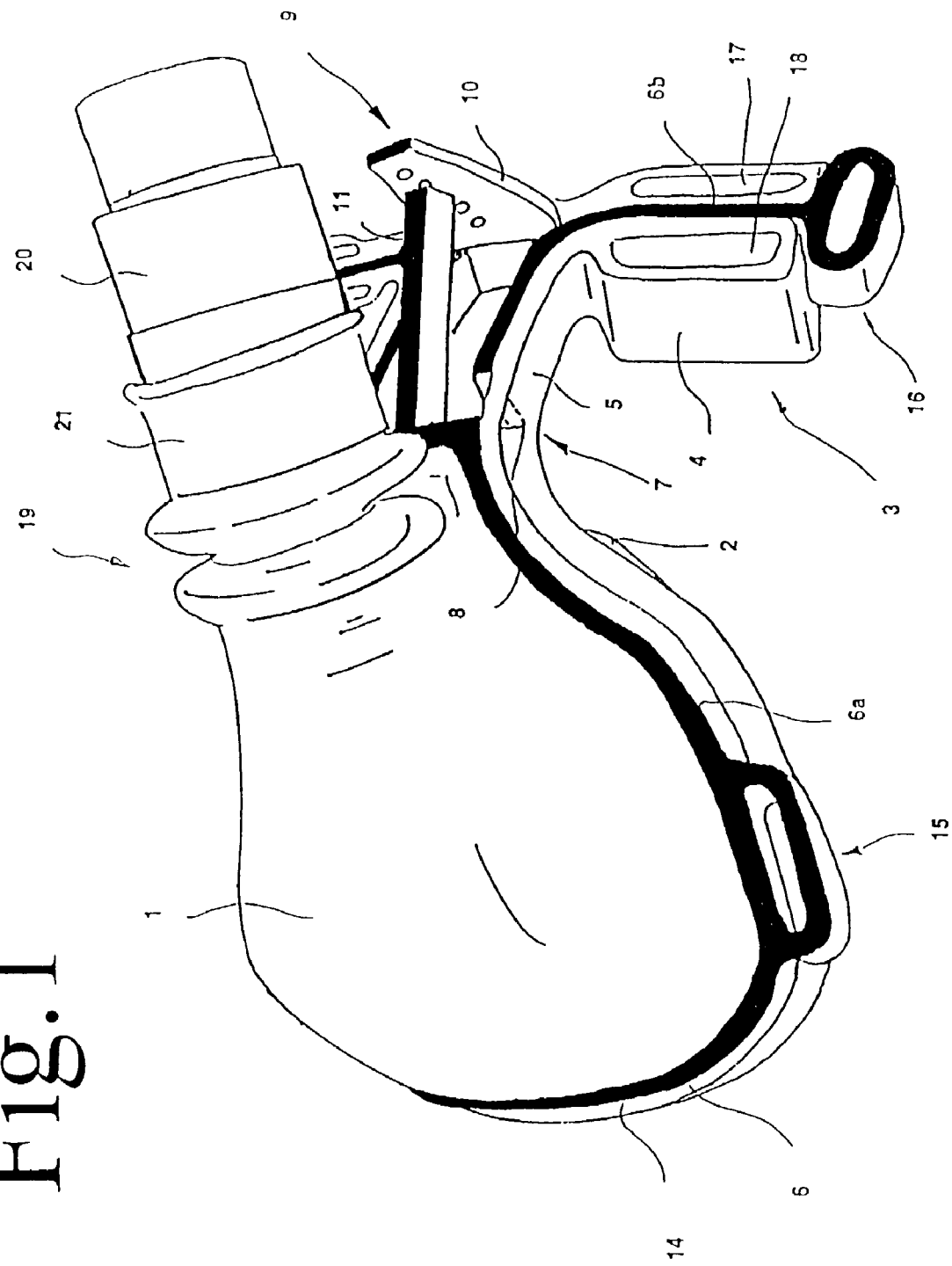
FIG. 1 shows a perspective view of a preferred embodiment of a breathing mask comprising an elastomer mask base body and an integral forehead rest means, wherein a reinforcement element is provided through which the position of the forehead rest means is adjustably variable relative to a sealing lip means that is formed integral with the forehead rest means.

The view according to FIG. 1 shows a breathing mask, as it may in particular be used for carrying out a CPAP therapy. The breathing mask comprises a mask base body 1, which in the embodiment shown is formed of a fully transparent elastomer silicone material. The mask base body 1 defines an interior of the mask sufficiently dimensioned for the accommodation of the nose of the user of the mask. The sealing of the interior of the mask space with respect to the facial surface of the user of the mask is carried out via a sealing lip means 2, which in this view is almost fully covered. The sealing lip means 2 comprises a sealing lip formed of an elastomer material, which rests on the half of the face of the mask user under elastic deformation and which defines a nose accommodation opening through which at least the nose tip area of the user of the mask may reach the mask interior defined by the mask base body 1.

The breathing mask is provided with a forehead rest means 3, which in this case comprises a forehead padding means 4. The forehead padding means 4 is in the embodiment shown also made of an elastomer material and is also formed integrally with the sealing lip means 2 and integrally with the mask base body 1. This integral design of mask base body 1, sealing lip 2 and forehead padding means 4 is achieved by forming a connection web section 5, which couples the forehead padding means 4 with the mask base body 1 in a manner that the position can be changed. In the circumferential portion of the mask body 1, a reinforcement element 6 is provided, which in this case is formed as a frame-like structure. The reinforcement element 6 comprises a first reinforcement section 6a following the circumferential contour of the sealing lip means 2 and a second reinforcement section 6b extending into the forehead rest means 3. The two reinforcement sections 6a, 6b are coupled in a manner movable with respect to each other. The coupling of the two reinforcement sections 6a, 6b, is implemented in the embodiment shown by a hinge means 7, which in this case is formed by a film hinge section 8. The relative position of the forehead padding means 4 relative to the mask base body 1 or to the sealing lip means 2 produced by pivoting the two reinforcement sections 6a, 6b with respect to each other, may permanently be defined via the fixing means 9.

The fixing means 9 in this case comprises a fixing element 10, which can be engaged with a holding element 11 in different fixing positions.

In the embodiment shown, the holding element 11 is substantially rigidly connected to the first connection section 6a. The fixing element 10 is pivotally connected to the second reinforcement section 6b. The coupling of the fixing element 10 and of the holding element 11 in selected coupling positions is carried out in this case via plug bores 12, which are formed in the fixing element 10. These plug bores 12 can be engaged with a fixing pin that cannot be seen in this case. The fixing pin is formed at a front end face of the holding element 11 facing the fixing element 10. As an alternative to the mechanism shown here, it is also possible to use other mechanisms for defining the relative position of the first reinforcement section 6a with respect to the second reinforcement section 6b.

The reinforcement means 6 is coupled to the mask base body 1 in a manner that the mask base body 1 and also the sealing lip means 2 have a shape also determined by the reinforcement element 6. In the embodiment shown, the coupling of the reinforcement element 6 with the mask base body 1 is performed by a circumferential groove 14 into which the frame-like reinforcement element 6 is inserted. For an improved coupling of the reinforcement element 6 with the mask base body 1 or with the sealing lip means 2, the circumferential groove is profiled in the area of the inner surfaces of the grooves complementary to the reinforcement element 6.

The reinforcement element 6 is provided with a coupling means 15 through which a band element below a head band arrangement can be coupled to the breathing mask. In the embodiment shown, the coupling means 15 is formed as a bracket-like flap, which is formed integrally with the reinforcement element. As an alternative, it is also possible to use constructively differently built coupling elements, e.g. catch or snap means for coupling the head band with the reinforcement element 6. By the direct introduction of the tensile forces of the head band into the reinforcement element 6 an inadmissible deformation of the mask base body 1 and of the sealing lip 2 is avoided.

In the area of the forehead rest means 3 a coupling means 16 is also provided, which in the embodiment shown basically corresponds to the coupling means 15 provided in the area of the mask base body 1.

The reinforcement element 6 or its second reinforcement or frame section 6b formed in the area of the forehead rest means 3 is connected with the forehead padding means 4. In the embodiment shown, the coupling of the forehead padding means 4 with the second reinforcement section 6b is implemented similar as the coupling of the first reinforcement section 6a with the mask base body 1 in that the second reinforcement section 6b is inserted into a groove formed in the forehead padding means 4.

The forehead padding means 4 is formed of an elastomer material and comprises a plurality of pocket sections 17, 18. The padding properties of the forehead padding means 4 may be influenced in a defined manner by the pocket sections 17, 18.

A bellows structure 19 is provided on the mask base body 1 through which a breathing hose connection adapter 20 is pivotally coupled with the mask base body.

The bellows structure 19 in the embodiment shown is also formed integrally with the mask base body 1, which prevents the possible generation of gaps in a manner that is advantageous in terms of hygiene. A hose pin section 21 is connected to the bellows structure 19, said hose pin section being dimensioned regarding its inner diameter in a manner that the breathing hose connection adapter 20 can be inserted therein in a fixedly seated manner. Instead of the breathing hose connection adapter 20, it is also possible to provide a $CO_2$ rinse adapter, as it is described in the applicant's German patent specification 198 40 760.2.

Figure 2:
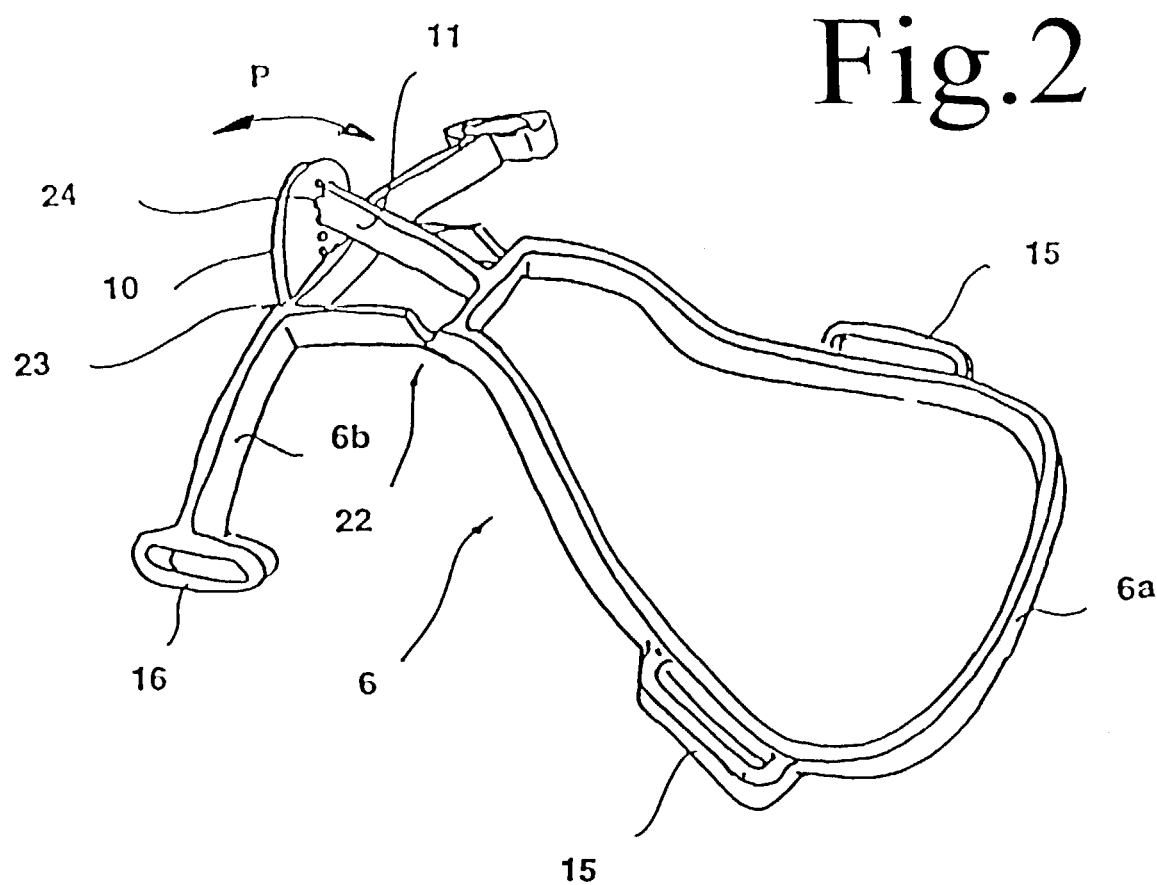
FIG. 2 shows a perspective view of a frame-like reinforcement element, as it is provided in the embodiment according to FIG. 1.

FIG. 2 shows the reinforcement element 6 in detail provided in the breathing mask according to FIG. 1. The first reinforcement section 6*a* assigned to the mask base body 1 of the breathing mask as well as the second reinforcement section 6*b* associated to the forehead rest means 3 (FIG. 1) are formed in this case by web-like elements, which have a substantially polygonal, in particular rectangular cross section. The coupling means 15, 16 already explained in connection with FIG. 1 are formed integrally with these web-like elements. In this view the coupling point formed in this case as a film hinge 22 can clearly be seen for coupling the two reinforcement sections 6*a*, 6*b*. The fixing element 10 is also supported via a film hinge portion 23 in a manner that, as shown by arrow P, it is pivotal in a sufficient angular range. By pivoting the fixing element 10 it is achieved that this fixing element releases a fixing pin 24, which is formed in the end portion of the holding element 11. As long as the fixing element 10 is not coupled to the holding element 11, it is possible to pivot the second reinforcement section 6*b* relative to the first reinforcement section 6*a* into a desired position. By engaging the engagement structure provided at the fixing element 10 with a corresponding complementary engagement structure of the holding element 11, it becomes possible to fix the two reinforcement sections 6*a*, 6*b* in the desired relative position with respect to each other. The fixing element 10, the holding element and the section of the second reinforcement element 6*b* extending between the film hinge 22 towards the film hinge 23 form, in the embodiment shown, a triangular structure, through which the relative position of the second reinforcement section 6*b* relative to the first reinforcement section 6*a* can be defined in an adjustable manner. As an alternative to this coupling structure that can be manufactured in a particular advantageous manner, it is also possible to use deviating coupling structures for coupling the two reinforcement sections 6*a*, 6*b*.

The first reinforcement section 6*a* comprises in the embodiment shown a substantially saddle-like outer contour. In a direction perpendicular with respect to the mask rest surface, the first reinforcement section 6*a* is drawn upwards in the nose bridge portion in a manner that this nose bridge portion does not fall below a predetermined minimum distance to the face half of the user of the mask.

Figure 3:
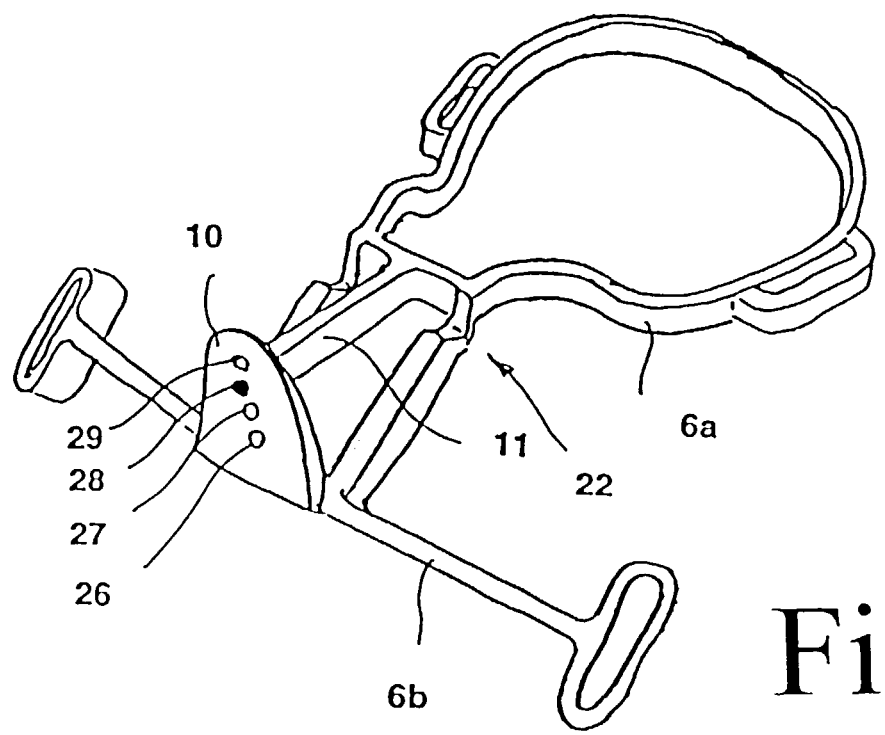
FIG. 3 shows a further perspective view of said reinforcement element, here with a view onto a fixing member that can be locked in a plurality of fixing positions.

FIG. 3 shows the mask frame according to FIG. 2 in another perspective. The fixing element 10 in this case comprises four catch bores 26, 27, 28 and 29.

The fixing element 10 is coupled with the holding element 11 in a manner that the catch bore 29 can be engaged with the fixing pin 24 of the holding element 11. When coupling the fixing element 10 with the holding element 11 by using the catch bore 29, the second reinforcement section 6*b* is pivoted towards the forehead portion of the user of the mask in a manner that the portion of the first reinforcement section 6*a* traversing the nose bridge is lifted up to the greatest extent. By selecting the catch bore 28 a configuration is chosen, in which the portion of the first reinforcement section 6*a* traversing the nose bridge is already approximated to the nose bridge of the patient. Even flatter configurations are obtained by the catch bores 27 and 26.

It is possible to introduce an adhesive in the area of the coupling element formed as a film hinge 22 in this case between the two reinforcement sections, which causes the relative position of the two reinforcement sections 6*a*, 6*b* to be durably fixed with respect to each other. The fixing element 10 and possibly also the holding element 11 may be removed after curing of the adhesive material. The adjustment of the breathing mask is performed in an advantageous manner by using the fully assembled breathing mask. It is also possible to adapt the reinforcement element in the disassembled state to the face structure of the user of the mask and to subsequently couple it to the mask base body. In an advantageous manner, further adjustment alternatives are provided, though which for instance the position of the forehead padding means can be adjusted in vertical and/or horizontal direction. As an alternative to the formation of the coupling portion between the two reinforcement sections as a hinge point, it is also possible to provide coupling alternatives through which for instance an adjustment alternative of the two reinforcement elements 6*a*, 6*b* e.g. by the supply of heat, is given.

Figure 4:
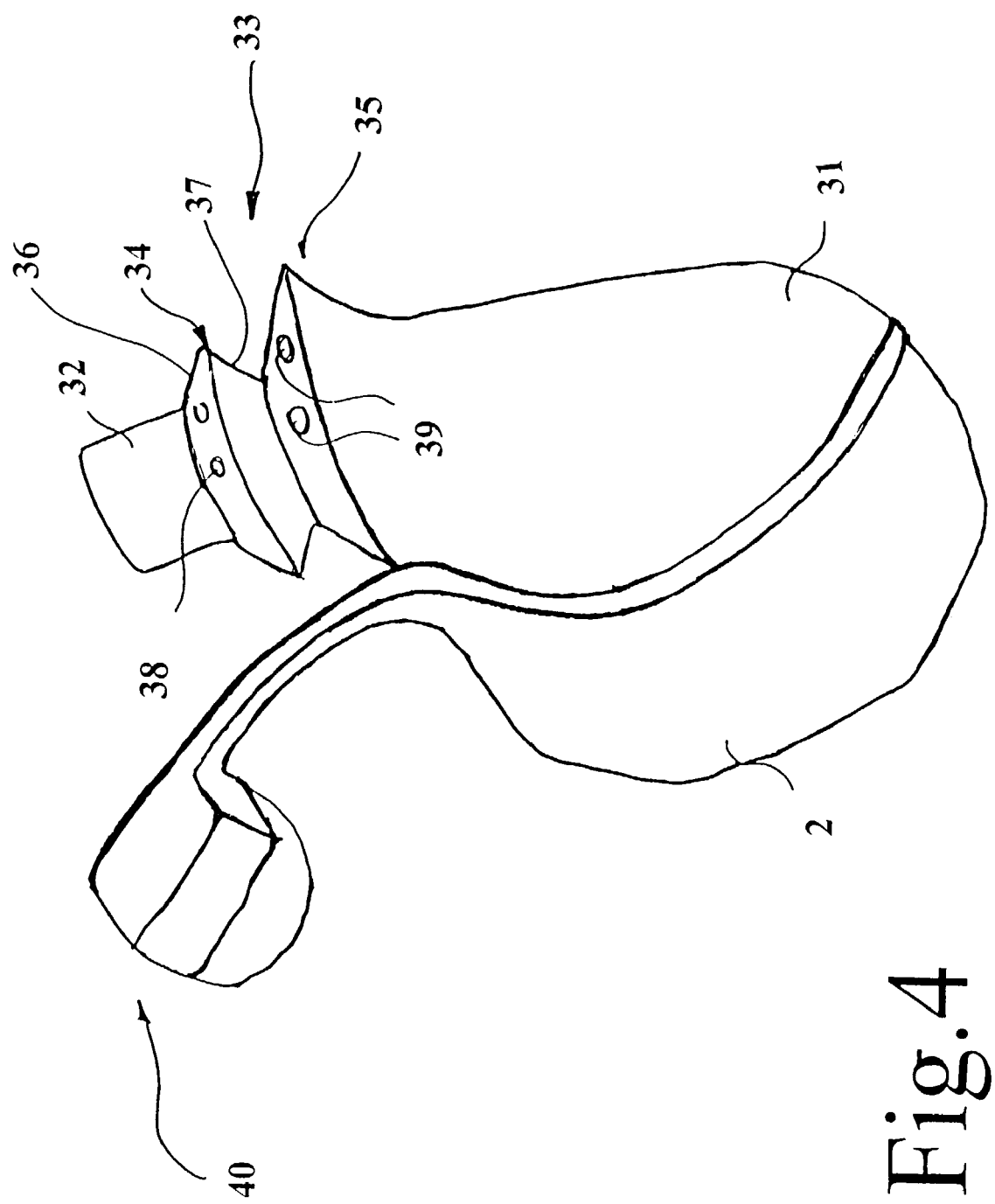
FIG. 4 shows a simplified perspective view of a further embodiment of a breathing mask with an elastomer de-coupling structure formed in the area of the breathing gas conducting means.

The breathing mask shown in FIG. 4 comprises a connection means 32 integrally formed with the mask base body 31 for a breathing gas line (not shown). In a transitional area between the connection means 32 and the mask base body 31, a de-coupling structure 33 is provided, which is formed in the embodiment shown by a bellows means. The bellows means comprises a first fold collar 34 and a second fold collar 35. In particular the first fold collar 34 comprises two circumferential walls 36, 27 extending in the radial direction. These two circumferential walls 36, 37 are formed as surfaces forming the envelope of a cone, and have a wall thickness distribution selected in view of a predetermined system rigidity. The de-coupling structure is formed rotational-symmetrical. An especially large breathing gas passage cross section at a comparatively small disturbance of the field of vision is achieved in an advantageous manner in that the breathing gas line section in the area of the nose bridge has an elliptical or polygonal cross section. The de-coupling structure is in this case formed in a rotational-symmetrical manner. As an alternative it is also possible to form the flanks of the fold collars in a manner that they have different depths and possible changing wall thickness in the circumferential direction.

In the embodiment shown, at least one breathing gas passage opening 38 is formed in the circumferential wall 36 facing the forehead portion of the mask user in the application position of the breathing mask. Through this breathing gas passage opening, a discharge of at least partially used breathing gas to the atmosphere can take place. In the area of the second fold collar 35 a plurality of breathing gas passage openings 39 are formed through which a breathing gas discharge can also take place across the forehead portion of the user of the mask. The breathing gas passage openings 38 and 39 are aligned in a manner that breathing gas exiting therefrom does not directly collide with the wall sections of the de-coupling structure or the connection means. The breathing gas passage openings 38 are preferably arranged in a manner that the air exiting cannot hit the forehead portion of the user of the mask.

It is also possible to form the de-coupling structure in a manner that an abutment characteristics is achieved so that a de-coupling is only permitted within a predetermined area of movement.

In the breathing mask shown in this case, a forehead rest means 40 integrally formed with the mask base body 31 is shown. The sealing lip means 2 for sealing the face rest zone is also formed integrally with the mask base body 31 or it is formed integrally with the forehead rest means 40 in the embodiment shown. The position of the forehead rest means 40 with respect to the mask base body 31 or with respect to the sealing lip means 2 is variable by means of an adjustment means.

Figure 5:
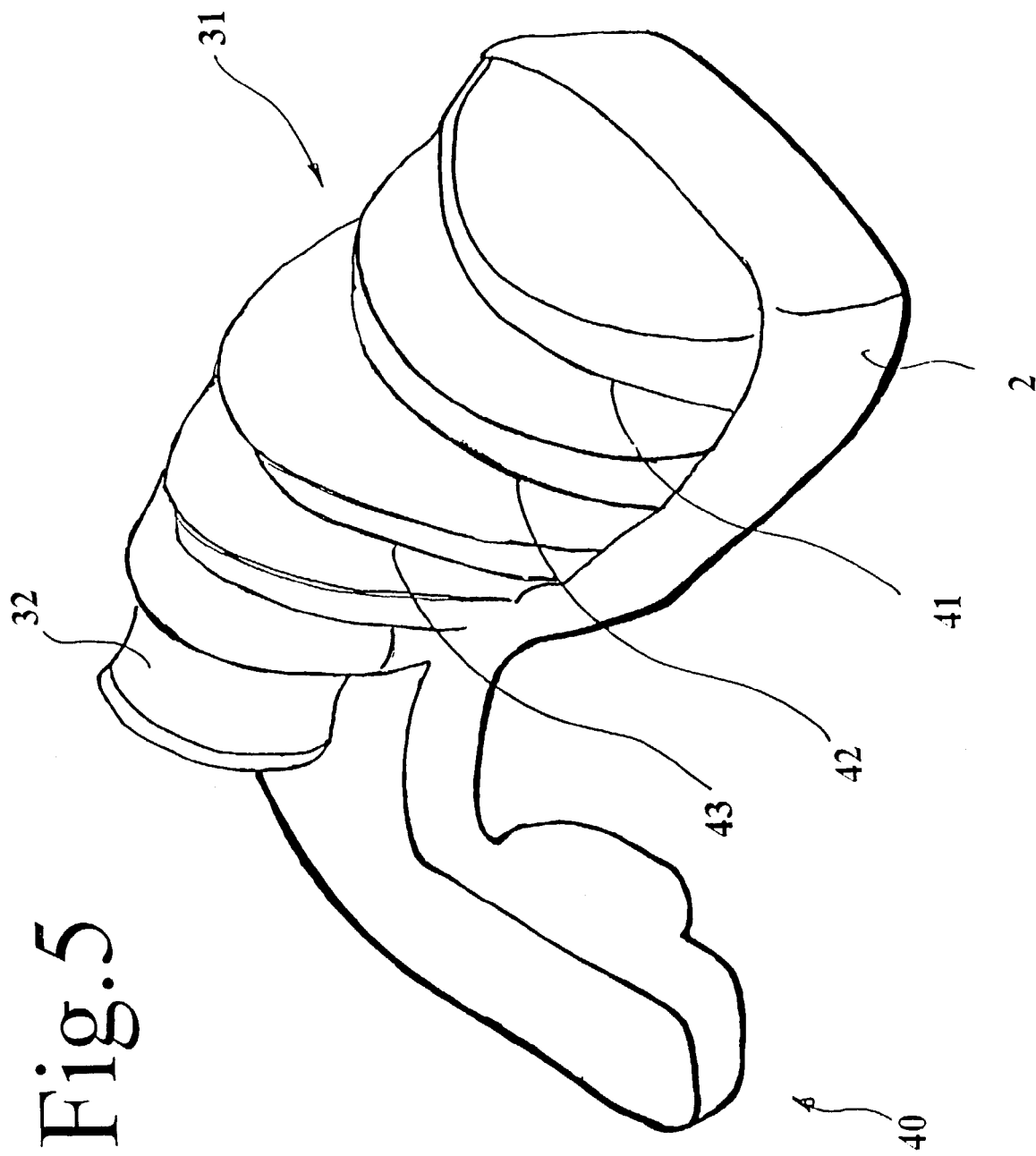
FIG. 5 shows a perspective view of a third embodiment of a breathing mask comprising a mask base body formed of an elastomer material, and a de-coupling structure formed at the mask base body, said de-coupling structure being formed by bellows.

In the embodiment of a breathing mask shown in FIG. 5, the mask base body 31 is also formed of an elastomer material, but contrary to the above-described embodiment it is provided with a plurality of folds, through which a substantially mechanical de-coupling of the connection means 32 from the sealing lip is achieved. In this embodiment, the breathing mask also comprises a forehead rest means 40, which similar to the above-described embodiment may be formed integrally with the mask base body 31.

The folds 41, 42, 43 are aligned in a manner that they bridge over the nose bridge portion in an arc-like manner in application position of the breathing mask. As an alternative to the embodiment shown with three comparatively deep folds, it is also possible to provide the mask base body 31 with a larger amount of corresponding folds, wherein the elastic properties of the individual folds are preferably adapted in a manner that predetermined properties with respect to the coupling of the connection means 32 and the sealing lip means 2 result.

Figure 6:
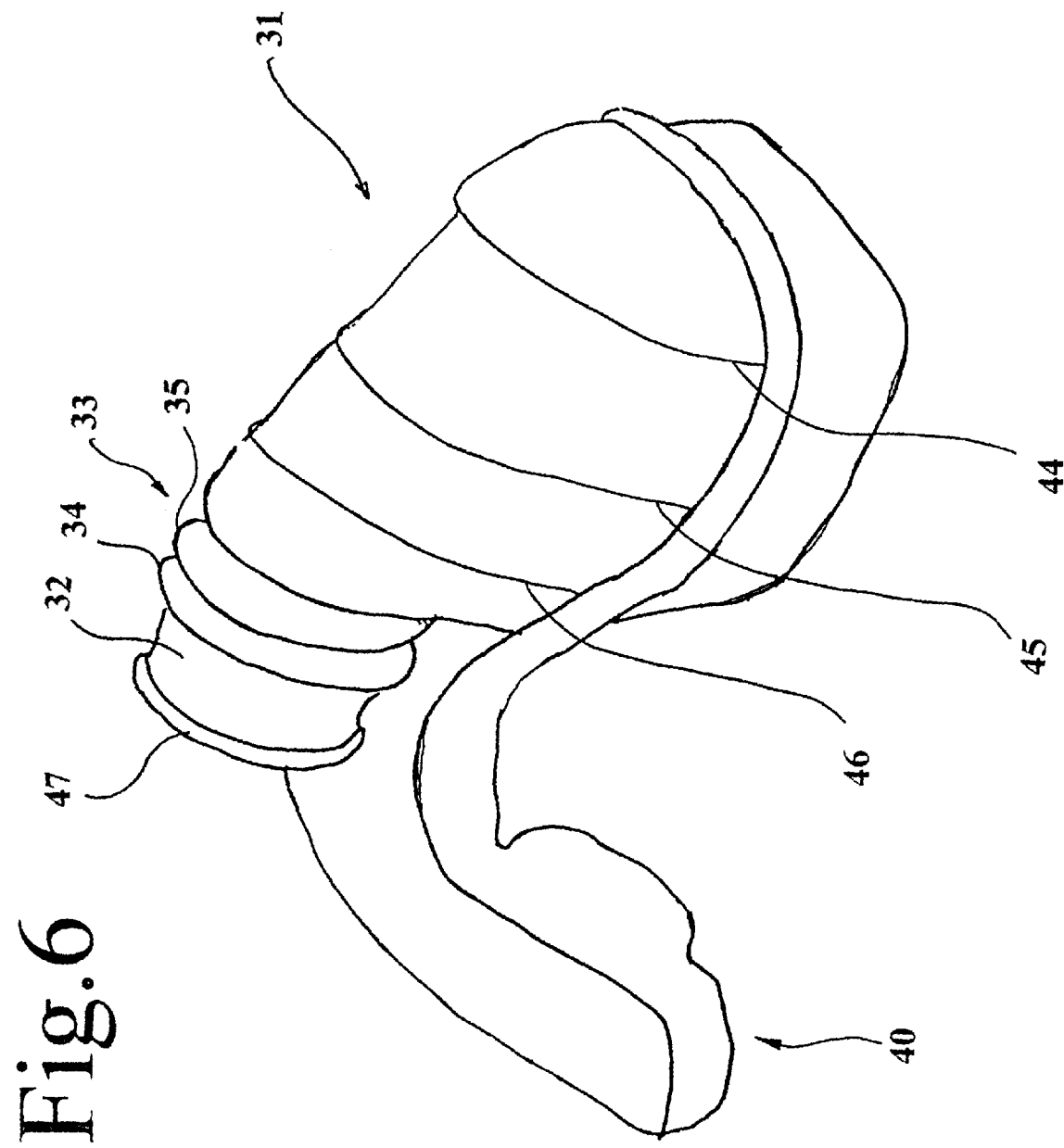
FIG. 6 shows a perspective view of a fourth embodiment of a breathing mask, also comprising a mask base body formed of an elastomer material, however, having a de-coupling structure formed according to the roller bellows principle.

The breathing mask shown in FIG. 6 comprises, similar to the above-described breathing mask, a de-coupling structure formed in the area of the mask base body 31. In the embodiment shown, the de-coupling structure is formed by a plurality of roller bellows zones 44, 45, 46. In addition to these roller bellows zones 44, 45, 46, a further de-coupling structure 33 is provided in the area of the connection means 32, which similar to the embodiment described in FIG. 4, comprises two fold collars 34, 35.

The support of this breathing mask in the forehead portion of a user of a mask is in this case also implemented by a forehead rest means 40 which in this case is formed integrally with the mask base body 31.

The connection means 32 in this case is formed integrally with the mask base body 31 and is also made of an elastomer material. The connection means 32 comprises a circumferential bead 47 through which an improved coupling with a breathing as line is achieved.

Figure 7:
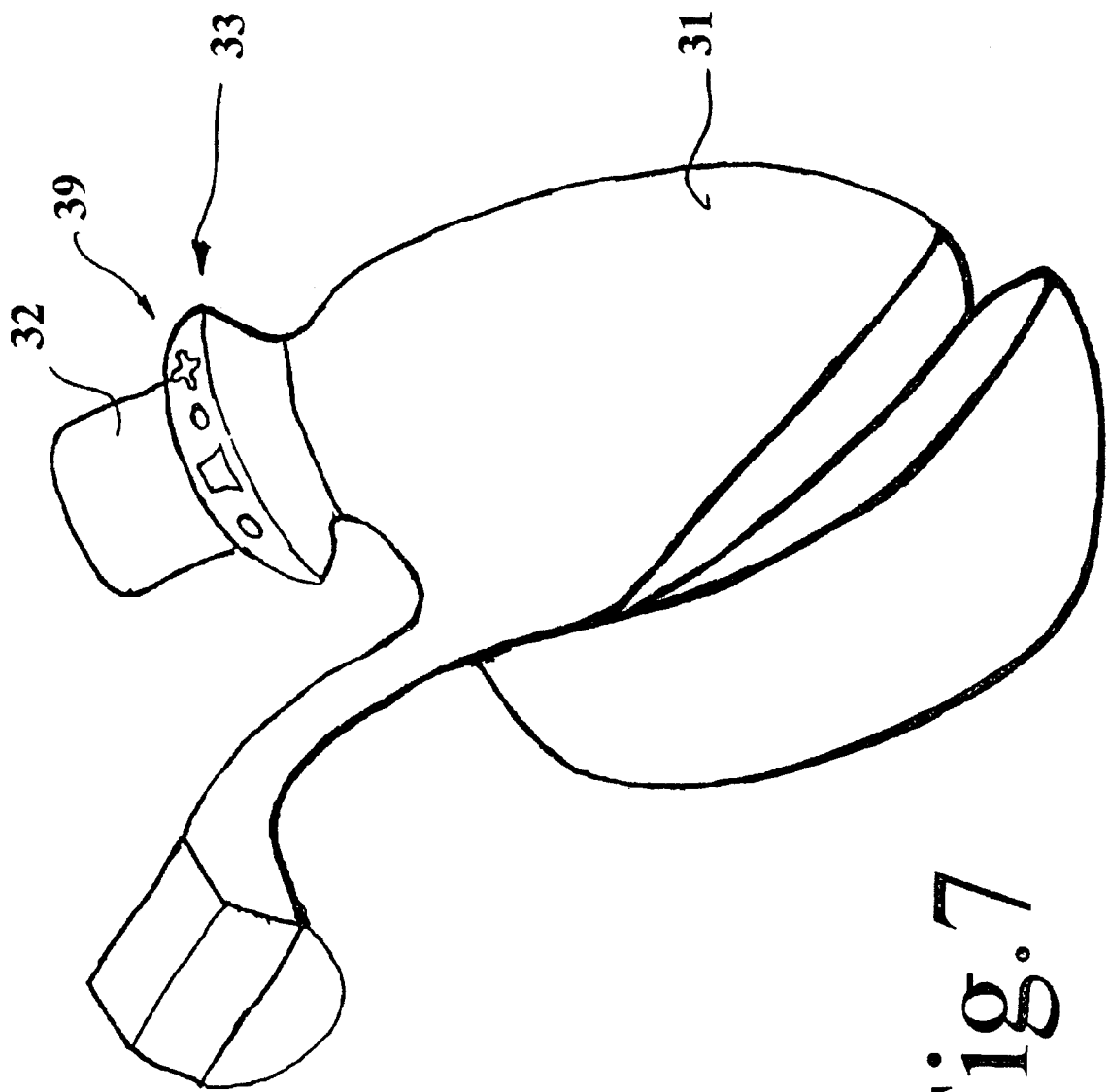
FIG. 7 shows a side view of a fifth embodiment of a breathing mask, also comprising a mask base body formed of an elastomer material, and a connection means for the breathing gas line connected thereto, wherein a de-coupling structure is formed between the connection means and the mask base body and in the area of the sealing lip means.

The breathing mask shown in FIG. 7 comprises a mask base body 31 made of an elastomer material having a connection means 32 that is also made of an elastomer material. The connection means 32 is formed integrally with the mask base body, wherein a de-coupling structure 33, in this case formed by one single bellows, is formed in a transitional portion of the connection means 32 in the mask base body 31. A plurality of breathing gas passage openings 39 are formed in the area of the de-coupling structure for discharging breathing gas from the interior of the mask defined by the mask base body 31. The breathing gas passages 39 have channel cross sections formed with respect to a predetermined discharge flow behavior. The breathing gas passages 39 may, as shown as an example, not only have round cross sections, as explained above, but they also may have polygonal, cross-shaped or other arbitrarily chosen geometries. The breathing gas passage openings are, however, preferably formed in a manner that the air flow therethrough is not directed towards the forehead portion of a user of a mask, but that it is directed in the hose direction in particular along the side of the hose wall opposite to the user of the mask.

Figure 8:
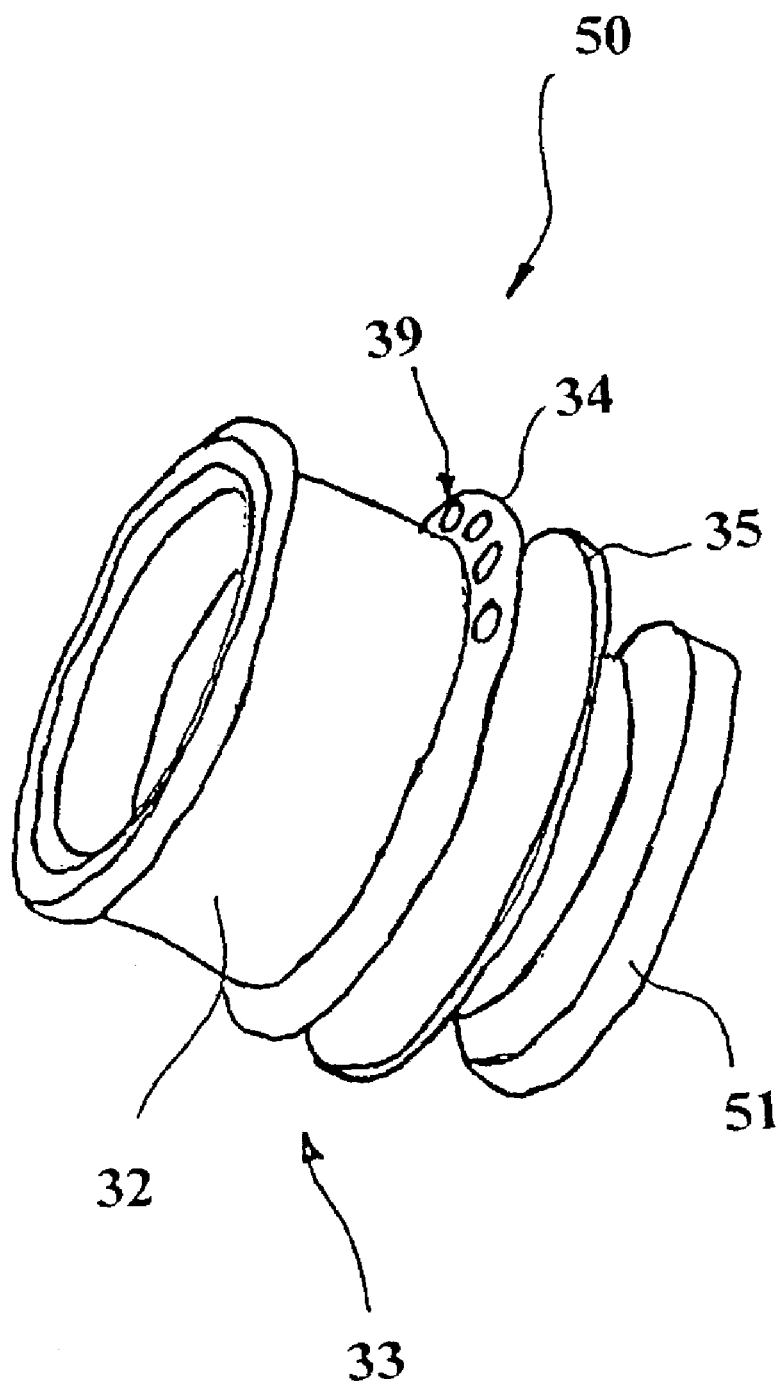
FIG. 8 shows a preferred embodiment of a connection section for a breathing gas line with integrated gas discharge openings.

FIG. 8 shows a discharge means 50 for discharging breathing gas. The discharge means 50 in this case forms a connection means 32 for connecting a breathing gas line and a de-coupling structure 33, which in this case comprises a plurality of fold collars 34, 35. On a side opposite to the connection means 32, the discharge means 50 is provided with an attachment structure 51 through which the discharge means 50 can be coupled in a sealing manner to a mask base body of a breathing mask or with a further breathing gas coupling section. Breathing gas passages 39 through which a discharge of breathing gas from the interior defined by the discharge means 50 to the atmosphere can take place are formed in an area of a circumferential section of the first fold collar 34 extending at an angle of approx. 120°.

Figure 9:
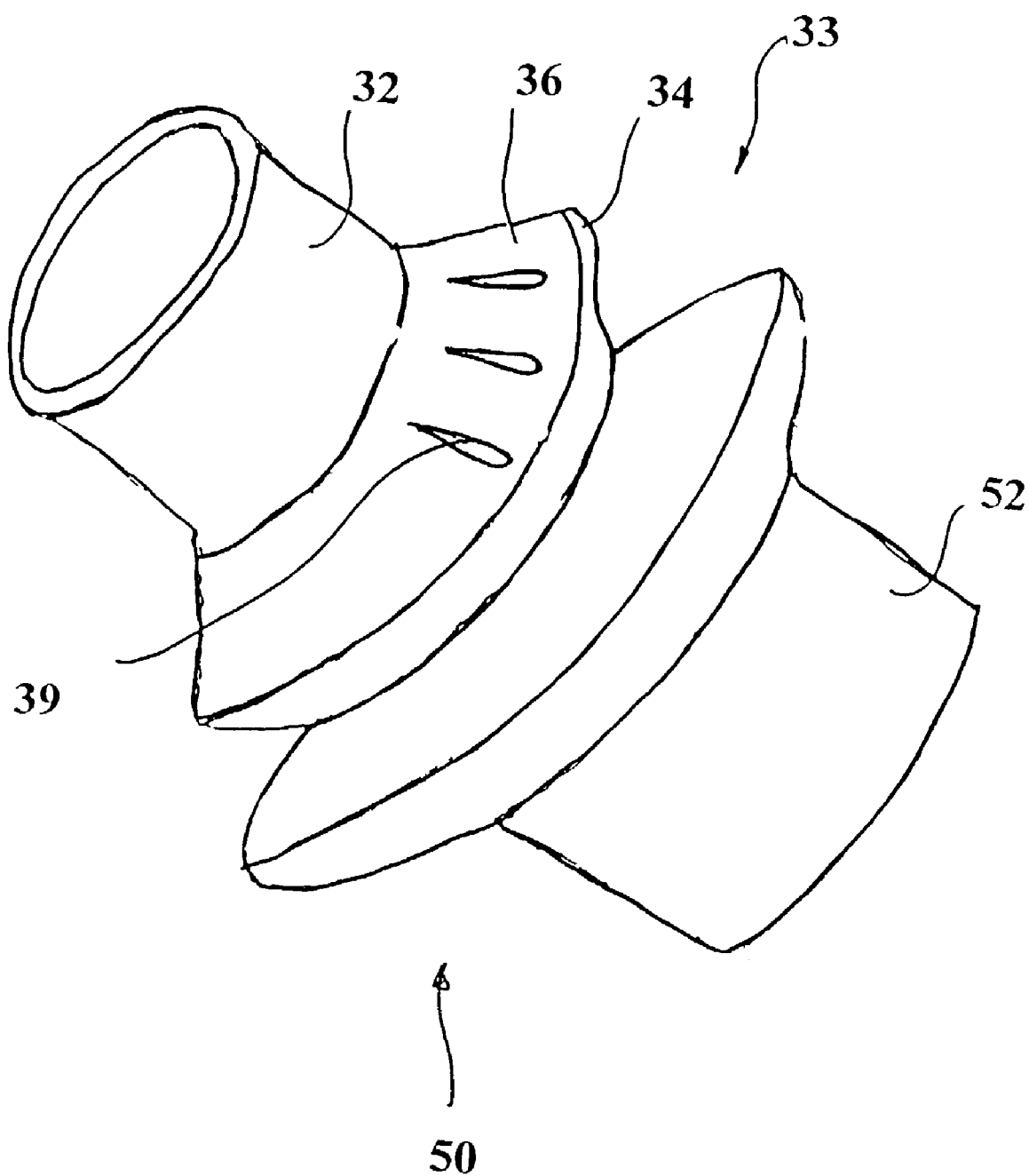
FIG. 9 shows a perspective view of a further embodiment of a connection means for a breathing gas line with a plurality of circumferential bellows and integrally formed discharge openings.

FIG. 9 shows a further embodiment of a discharge means 50 for discharging at least partially used breathing gas. The discharge means 50 comprises a connection means 32 provided for connecting a breathing gas line, and a connection structure 52 formed on the side opposite to the connection means 32, through which said connection structure the discharge means can be coupled to the mask base body 31 or to a further breathing gas line section. A de-coupling structure 33 is provided between the connection structure 52 and the connection means 32, through which a relative movement between the connection means 32 and the connection structure 52 in a predetermined area of movement is admitted. In the embodiment shown, axial movements in an area of movement of up to 10 mm and tilt movements in an angular range of approx. 30° are allowed. In a circumferential section of a circumferential wall 36 of the first fold collar 34, breathing gas passage openings 39 are formed similar to the above-described embodiment. The breathing gas passage openings 39 are formed as narrow, substantially radially aligned slots. The wall thickness of the circumferential walls of the two fold collars 34 are chosen thinner in the area of the fold portions than in the wall portion extending between the fold portions. The embodiment of a discharge means shown comprises in the area of the connection means 32 an inner diameter of 18 mm and in the area of the de-coupling structure 33 an outer diameter of 35 mm. The axial length of the discharge means 50 is 54 mm in unloaded condition. The discharge means 50 is formed of an elastomer material—in this case a fully transparent silicone rubber. The maximum wall thickness of the discharge means 50 is 4 mm.

FIG. 10 shows the sketch of a preferred embodiment of a channel means for discharging breathing gas. The breathing gas path defined in this case extends through a passage opening 53 in a first intermediate chamber 54, which communicates with the atmosphere via a gap portion 55. A plurality of web portions 56 are formed in this gap portion, through which said web portions the throttle characteristics of the gap portion are influenced. The flow behavior of the breathing gas path can be influenced in a defined manner by the length of the gap portion 55 in particular in connection with the webs 56. Such a breathing gas path for discharging breathing gas from a mask interior to the atmosphere can directly be formed in the area of a connection means for connecting a breathing gas line. The structure shown in this case is preferably formed integrally of a fully elastomer material. For cleaning purposes it is possible to turn up an upper lid wall 57 towards the top. A required minimum gap measure in the gap portion 55 can be achieved by web sections that are not shown, which extend section-wise up to the inner surface of the lid wall 57.

FIG. 11 shows an elastomer structure, which in connection with a breathing mask is directly suitable for display of the deformation taking place when applying the breathing mask. It is for instance possible to provide a color mark in the area of the inner wall of a fold or bellows structure 60, said color mark becoming visible depending on the deformation of the fold or bellows structure. If for instance the fold or bellows structure 60, as shown in FIG. 11, is upset at a maximum, the color mark arranged in the area of the inner wall of the fold or bellows structure can no longer be seen from the outside. This results for instance in an inadmissibly high surface pressure in the area of the forehead rest and/or in the area of the sealing lip means of a correspondingly designed breathing mask. It is also possible to check by means of such a fold or bellows structure 60, whether a sufficient mask holding force is exerted onto the breathing mask. In such an embodiment, the colored mark can for instance be arranged in a manner that it is visible in the case of insufficient mask holding forces and is covered when the mask holding forces are sufficient.

Figure 12:
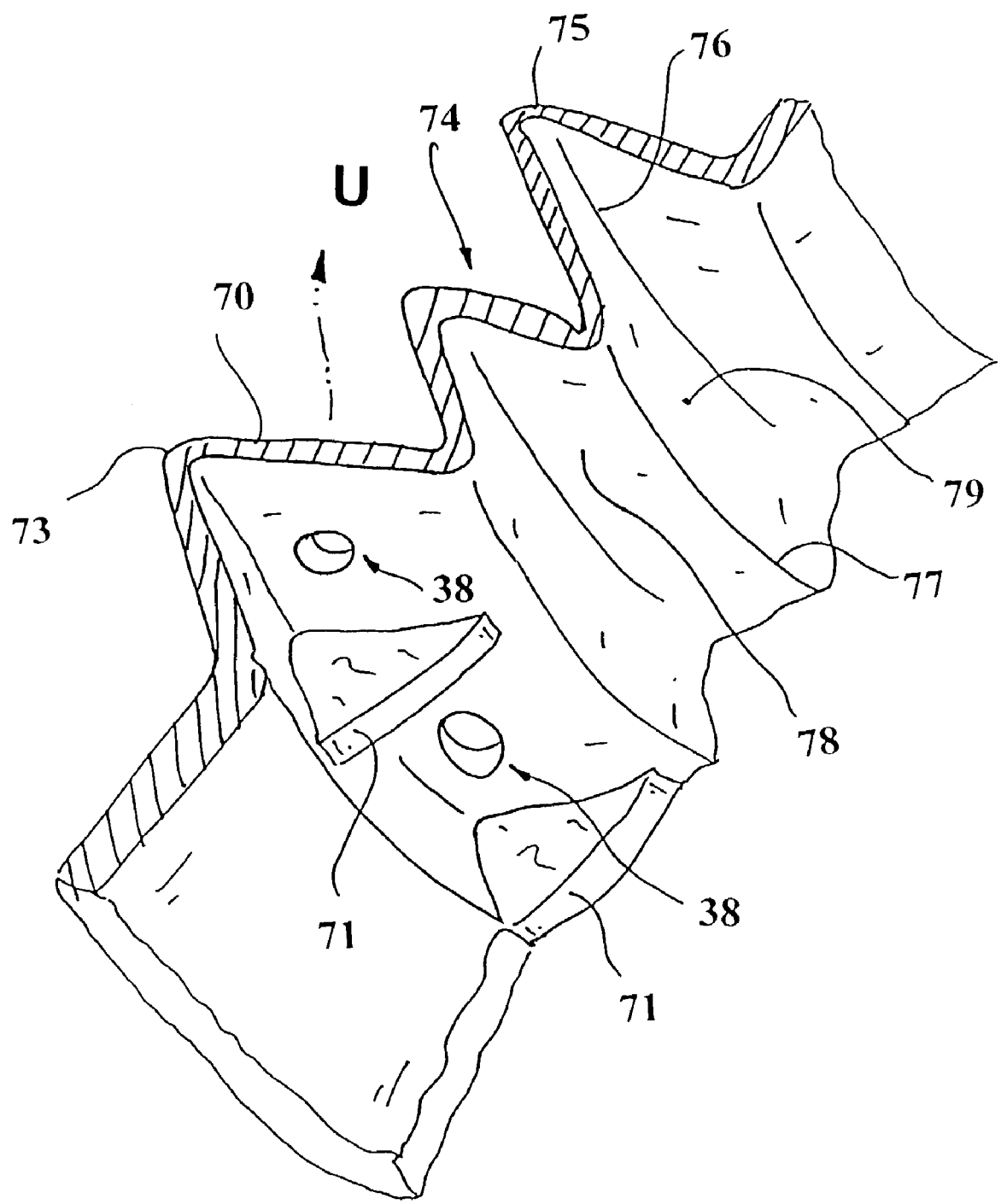
FIG. 12 shows a detailed sketch for explaining a preferred embodiment of reinforcement webs for preventing a locking of the passage openings.

FIG. 12 shows a section of a discharge means for discharging breathing gas, which is formed of an elastomer material. The discharge means comprises a circumferential wall 70, formed in this case as a fold collar 73. The circumferential wall is provided with a plurality of passage openings 38 for discharging breathing gas. Webs 71 are formed in the interior of the fold collar 73, said webs being formed integrally with the circumferential wall 70. The webs 71 act as a fold safety means and ensure that the passage openings 38 are open permanently. A division of the gas flow is further achieved by the webs 71, which leads to a low-noise discharge of the breathing gas to the atmosphere (U). The passage openings in this case have a circular cross section. A further fold collar 74 is connected to the fold collar 73 that is provided with the passage openings 38. This fold collar 74 is comparatively rigidly coupled with the first fold collar 73 and also has a small height so that a covering of the passage opening 38 by a further fold collar 74 is not possible. A hinge fold collar 75 is connected to the further fold collar 74. This hinge fold collar defines a circumferential hinge zone 76 in the area of its maximum diameter and an inner hinge zone 77 in the inner portion. In the area of the inner hinge zone 77 and the circumferential hinge zone 76, the wall thickness of the circumferential wall 70 is formed so small that a comparatively easy movability of the two sections of the discharge means opposing each other is given. The circumferential walls 78 of the fold collar 74 and the circumferential wall 79 of the hinge fold collar 75 together restrict the maximum pivot angle of the two fold collars with respect to each other.

The function of the above-described breathing mask is not described in detail by means of the following example.

To carry out a CPAP therapy, the breathing mask is removed from a sterile packaging, and the fixing element 10 is pivoted into a release position so that the reinforcement section 6b can be pivoted with respect to the first reinforcement section 6a around the film hinge point. A breathing gas hose is connected to the breathing mask via a rotary or quick-snap adapter, in that this breathing gas hose is connected to the quick-snap adapter and this quick-snap adapter is inserted into the breathing hose connection adapter 20. Breathing gas at a predetermined excess pressure of e.g. 8 mbar is supplied via the breathing gas hose. Now the breathing mask is applied onto the nose portion of the user of the mask. For this purpose, a lower head band arrangement is passed through. The tensile stress in the lower head band arrangement is adjusted in a manner that a sufficient tightness of the sealing lip means 2 is ensured. Now the breathing mask is tilted in the application position away from the nose back or towards the nose back until an optimal abutment of the sealing lip means 2 in the area of the nose back is achieved. Now the upper forehead padding means 4 is slightly pressed against the forehead of the user of the mask. The relative position of the first reinforcement section 6a achieved thereby is fixed relative to the second reinforcement section 6b, in that the fixing element 10 is engaged with the holding element 11.

As a result of the excess pressure prevailing in the breathing gas line, $CO_2$ flows through the passage openings formed in the fold collar The passage openings are dimensioned and formed in a manner that a predetermined pressure/volume characteristic is achieved so that a sufficient discharge of the breathing air exhaled into the breathing mask or into the breathing bas line to the atmosphere is achieved.

It is ensured by the webs formed in the fold bellows that the openings are not closed due to a compensation movement allowed by the de-coupling structure.

The breathing mask is now adjusted ready for use. By coupling the coupling means 16 in the area of the forehead rest means 3, the breathing mask is also fixed in the forehead portion of the user of the mask by the upper head band arrangement on the user of the mask.

It is possible to fix the relative positioning achieved in this case by additional measure e.g. an element blocking in a locking manner (e.g. safety element). If these additional fixing means are able to take a load it is possible to remove the fixing element 10 and possibly also the holding element 11.

It is also possible to chose a reinforcement element from a reinforcement element set by means of the ideal configuration of the breathing mask detected via the fixing means 9, which provides the desired relative position by renouncing the fixing means 9 of the sealing lip means and the forehead padding means 4, and to exchange such a reinforcement element by the above-mentioned reinforcement element.

The invention claimed is:

1. A breathing mask arrangement for delivering breathable gas to a patient, comprising:
   a frame having a mask retaining portion;
   a nasal mask having a body portion structured to be removably attachable to the mask retaining portion of the frame and a sealing portion structured to engage a patient's face generally along nasal bridge, cheek, and lip regions of the patient's face;
   a T-shaped forehead support having an upper cross portion and a lower leg portion, the upper cross portion of the forehead support extending along a first axis and supporting elastomeric forehead padding that is structured to engage a patient's forehead, the lower leg portion of the forehead support moveably coupled to the frame via a film hinge to allow movement of the forehead support relative to the frame about a second axis that is parallel to the first axis to thereby adjust the position of the forehead padding relative to the patient along an arcuate path;
   a conduit member in fluid communication with the nasal mask to deliver breathable gas into a nasal breathing space of the nasal mask;
   a hose connector coupled to the conduit member, the hose connector structured to be connected to a gas delivery tube; and an adjustment arrangement including at least four recesses and a projection, the recesses being adapted to receive the projection to positively lock the forehead support relative to the frame to allow selective adjustment of the forehead support relative to the frame, wherein the forehead support supports the forehead padding at an elevated position with respect to the film hinge when the forehead support is positively locked relative to the frame.

2. The breathing mask arrangement according to claim 1, wherein the upper cross portion of the forehead support includes a pair of coupling structures structured to be removeably connectable to an upper band arrangement of a headband assembly and the frame includes a pair of coupling structures structured to be removeably connectable to a lower band arrangement of the headband assembly for maintaining the mask arrangement in a desired position on a patient's face.

3. The breathing mask arrangement according to claim 2, wherein the body portion of the nasal mask includes a first interlocking surface that engages a second interlocking surface provided in the mask retaining portion of the frame when the nasal mask and the mask retaining portion are engaged with one another, the first and second interlocking surfaces interlocking with one another.

4. The breathing mask arrangement according to claim 1, wherein the recesses are provided on the forehead support and the projection is provided on the frame.

5. A breathing mask arrangement for delivering breathable gas to a patient, comprising:

a frame having a mask retaining portion;

a nasal mask having a body portion structured to be removably attachable to the mask retaining portion of the frame and a sealing portion structured to engage a patient's face generally along nasal bridge, cheek, and lip regions of the patient's face;

a forehead support supporting elastomeric forehead padding that is structured to engage a patient's forehead, the forehead support being moveably coupled to the frame via a film hinge to allow movement of the forehead support relative to the frame along an arcuate path to thereby adjust the position of the forehead padding relative to the patient;

a conduit member in fluid communication with the nasal mask to deliver breathable gas into a nasal breathing space of the nasal mask;

a hose connector coupled to the conduit member, the hose connector structured to be connected to a gas delivery tube; and an adjustment arrangement including at least four recesses and a projection, the recesses being moveable with movement of the forehead support along the arcuate path and being adapted to receive the projection to positively lock the forehead support relative to the frame to allow selective adjustment of the forehead support relative to the frame, wherein the forehead support supports the forehead padding at an elevated position with respect to the film hinge when the forehead support is positively locked relative to the frame.

6. The breathing mask arrangement according to claim 5, wherein an upper portion of the forehead support includes at least one coupling structure structured to be removeably connectable to an upper band arrangement of a headband assembly and the frame includes a pair of coupling structures structured to be removeably connectable to a lower band arrangement of the headband assembly for maintaining the mask arrangement in a desired position on a patient's face.

7. The breathing mask arrangement according to claim 6, wherein the body portion of the nasal mask includes a first interlocking surface that engages a second interlocking surface provided in the mask retaining portion of the frame when the nasal mask and the mask retaining portion are engaged with one another, the first and second interlocking surfaces interlocking with one another.

8. The breathing mask arrangement according to claim 5, wherein the recesses are provided on the forehead support and the projection is provided on the frame.

* * * * *